(12) United States Patent
Murch

(10) Patent No.: US 8,226,708 B1
(45) Date of Patent: Jul. 24, 2012

(54) INFLATABLE INTRALUMINAL GRAFT

(75) Inventor: Clifford Rowan Murch, Ayr (GB)

(73) Assignee: TriVascular, Inc., Santa Rosa, CA (US)

( * ) Notice: Subject to any disclaimer, the term of this patent is extended or adjusted under 35 U.S.C. 154(b) by 0 days.

(21) Appl. No.: 10/168,053

(22) PCT Filed: Mar. 3, 2000

(86) PCT No.: PCT/GB00/00732
§ 371 (c)(1),
(2), (4) Date: Jun. 14, 2002

(87) PCT Pub. No.: WO00/51522
PCT Pub. Date: Sep. 8, 2000

(30) Foreign Application Priority Data

Mar. 3, 1999 (GB) .................................. 9904722.7

(51) Int. Cl.
*A61F 2/06* (2006.01)
(52) U.S. Cl. ....................... 623/1.25; 623/1.27; 623/1.28
(58) Field of Classification Search .................. 623/1.25, 623/1.24, 1.27–1.28, 1.12, 1.22, 1.16
See application file for complete search history.

(56) References Cited

U.S. PATENT DOCUMENTS

| 5,156,620 | A | * | 10/1992 | Pigott | 623/1.25 |
|---|---|---|---|---|---|
| 5,292,362 | A | * | 3/1994 | Bass et al. | 106/173.01 |
| 5,545,135 | A | * | 8/1996 | Iacob et al. | 604/103.1 |
| 5,607,468 | A | * | 3/1997 | Rogers et al. | 128/898 |
| 5,693,088 | A | * | 12/1997 | Lazarus | 623/1.35 |
| 5,833,651 | A | * | 11/1998 | Donovan et al. | 604/509 |
| 6,004,347 | A | * | 12/1999 | McNamara et al. | 623/23.64 |
| 6,152,956 | A | * | 11/2000 | Pierce | 623/1.13 |
| 6,312,462 | B1 | * | 11/2001 | McDermott et al. | 623/1.25 |
| 6,395,019 | B2 | * | 5/2002 | Chobotov | 623/1.13 |
| 6,692,523 | B2 | * | 2/2004 | Holman et al. | 623/1.25 |

* cited by examiner

*Primary Examiner* — Thomas J Sweet
*Assistant Examiner* — Christopher D Prone
(74) *Attorney, Agent, or Firm* — Hoffmann & Baron, LLP

(57) ABSTRACT

A collapsible stent graft for aortic aneurysms includes a collapsible inner tubular member (26) and an outer layer (24) fused or adhered thereto such as to provide a spiral inflatable member (22) therebetween. The stent graft is inserted into an artery in the collapsed state and then expanded into position by introducing a liquid into the inflatable member and sealing the member. The graft is held in place by an expandable stent (40).

29 Claims, 3 Drawing Sheets

INFLATABLE INTRALUMINAL GRAFT

CROSS-REFERENCE TO RELATED APPLICATIONS

This application is the National Stage of International Application No. PCT/GB00/00732, filed Mar. 3, 2000, which claims the benefit of Application No. GB 9904722.7, filed Mar. 3, 1999.

TECHNICAL FIELD

This invention relates to intraluminal grafts. More particularly, this invention relates to intraluminal grafts useful as a lining for blood vessels or other body conduits.

BACKGROUND

Previously, the treatment of abdominal aortic aneurysms has involved using surgical grafts wherein the grafts are sutured into place. Conventional vascular grafts have long been used in humans and animals.

The treatment of abdominal aortic aneurysms requires a major surgical procedure to open the abdomen, excise the aneurysm sac and replace the vessel with a graft, which is sutured into place under direct vision. Many materials have been used to form the graft. At the present time this remains the preferred method of treatment for almost all abdominal aortic aneurysms.

Surgical graft materials such as flexible tubes of woven or knitted polyethylene terephthalate or porous polytetrafluoroethylene (PTFE) have previously been used. Grafts of biological origin have also been used; examples of these being fixed human umbilical or bovine arteries.

In the last few years, attempts have been made to reduce the extent of the surgical procedure by introducing these conventional, surgical grafts through the femoral arteries, passing them proximally, through the iliac arteries into the aorta and fixing them in place using endovascular stents, rather than sutures. These surgical grafts are large calibre devices which, even in their non-deployed state, are as large or even exceed the diameter of the iliac arteries through which they must pass. As the iliac arteries are often narrowed by, for example, atheromatous disease, the arteries may be damaged during introduction of the device.

More recently, interventional radiologists have attempted to improve on this concept using non-surgical graft material, catheters and endovascular stents to locate suitable vascular grafts or conduits onto the aortic aneurysm sac, from percutaneous punctures in the femoral arteries, requiring minimal surgical intervention. These techniques have become known as minimally invasive therapy.

A driving force to the development of the devices proposed in the present application has been the reduction in the size of the device when being inserted and also the reliability of the devices.

Although intraluminal devices are well-known in the field for the repair of inner linings for blood vessels or other body conduits, these previous types of devices are constructed, for example, from a thin layer of PTFE wrapped around a housing which is capable of expansion. Examples of such housings include self-expanding or balloon expandable-type devices comprising a mesh-like structure.

Due to the mesh-like structures used in previously known stent grafts, there is a minimum diameter to which the device can be reduced on its full contraction. On average, the minimum to which these devices can be reduced is 7 mm (21 French gauge) in diameter. There is therefore a limitation of these types of devices, for example, for use in babies, small children and old people where any amount of abrasion on the inner lining of the blood vessel during insertion of the stent graft may cause rupture of the vessel. It can also prove troublesome to expand these devices once inserted into the body. These types of grafts may also suffer from kinking which can result in the blocking of the passageway.

It is an object of at least one aspect of the present invention to mitigate one or more of the aforementioned problems and disadvantages of the prior art.

It is therefore an object of the present invention to provide a kink resistant device capable of forming a lining for blood vessels or other body conduits.

SUMMARY OF THE INVENTION

According to one aspect of the present invention, there is provided a collapsible stent graft which comprises a collapsible tubular member for lining a blood vessel and an inflatable member extending around the tubular member and attached thereto whereby inflation of the inflatable member expands the tubular member from a collapsed state to an expanded state wherein in use it lines the blood vessel.

By collapsible herein is meant that the stent graft is capable of collapsing into a structure with a smaller cross-sectional area.

A stent graft is a structure capable of forming a lining in a body conduit which can be firmly secured within the conduit via a stenting procedure. The stent graft may or may not include an actual stent.

Preferably, the inflatable member is formed by partially fusing or adhering an outer layer to the collapsible tubular member so as to provide one or more inflatable members therebetween. Alternatively, a separate continuous inflatable member is fused or adhered onto the outer surface of the tubular member. The inflatable member preferably forms a spiral structure comprising a plurality of turns around the tubular member. The inflatable member is preferably 1-2 mm in cross-sectional diameter with a spacing of 1-2 mm between adjacent turns of the inflatable member measuring along the longitudinal length of the stent graft.

The inflatable member may also take a variety of other shapes such as a zig-zag or square-wave pattern around the tubular member.

There may be a plurality of inflatable members around the collapsible tubular member.

Preferably, a tube is attached to the proximal end of the inflatable member to allow inflation thereof. A further tube may also be attached to the distal end to allow preferential inflation thereof to locate the graft in the desired place. Any free ends of the inflatable channel are, of course, closed. The tube(s) may be removably attached by known means (one-way valve, screw etc.) to allow removal after use in such manner as to maintain the channel in the inflated state. Alternatively, one or both tubes could be integrally formed between the tubular member and outer layer.

A removable sheath may be provided around the stent graft to facilitate insertion into an artery and which is removed prior to expansion of the stent graft.

The material for inflating the inflatable member is preferably a low viscosity liquid so as to be easily injected, is radio-opaque to assist visualisation of the graft in vivo, able to set to form a gel-like substance, give flexibility to the graft, be non-toxic and adhere to the inner and outer walls of the inflatable member to help prevent a tear of the inner layer causing dissection. Dissection is where the lining of the stent graft becomes torn and separated from the blood vessel leading to occlusion of the blood vessel and restriction in the flow of blood therein.

Suitable materials for inflation may be, for example, silicone-based liquids, elastomeric materials, plastics materials, or a thermoplastic or thermosetting resin mixture which may be solidified after injection. A chemically cured resin, such as cyanoacrylate resin ("superglue") may be used. A further suitable substance may, for example, be 2-hydroxyethyl methacrylate (HEMA). Silicone liquid satisfies some of the required criteria, but would not bond to the inner and outer surfaces of the inflatable member. However, this may not be a problem if polytetrafluoroethylene (PTFE) or other material sufficiently strong to resist tearing is used.

Any suitable length and diameter of collapsible tubular member may be used. The collapsible tubular member is of tubular shape generally with a thickness of at most 0.2 mm and preferably thinner than 0.1 mm and a cross-sectional diameter ranging from, for example, 25 mm to 30 mm. The collapsible tubular member may also be of a bifurcated form. The tubular member may also be tapered. In its collapsed state the tubular member has a small cross-sectional diameter.

Preferably, the end of the collapsible tubular member has an undulating shape which helps to maximise the contact between the graft and the aorta of the patient, so as to accommodate different levels of the origins of the renal arteries from the aorta. Alternatively, the end may be angled.

Hooks on the stent, not at the inflatable sites, (as used with a Gianturco stent) may also be desirable for fixing the stent graft in place. As PTFE is suitable for suturing, this is ideal for this form of fixation. Markers on the graft are preferred so that the correct part of the graft is used for stenting.

Preferably, the stent graft is introduced in a collapsed state into the body conduit via a small puncture therein using a catheter. Preferably, the graft is wound round a central catheter, with the catheter shaft of the angioplasty balloon used to distend the proximal aortic stent, which would pass over a guide wire introduced initially by arterial puncture in the groin.

Preferably, the inflatable and collapsible tubular member is made from expanded PTFE. Generally, the thickness of this sheet is at most 0.1 mm and preferably thinner. Uni-axially oriented films having a microstructure of uni-axially oriented fibrils wherein substantially all of the fibrils are oriented parallel to each other may be used. Multi-axially oriented films having a microstructure of bi-axially or multi-axially oriented fibrils wherein the fibrils are oriented in at least two directions which are substantially perpendicular to each other may also be used.

If the graft is made of an inner and outer layer fused together and the inner layer is made of expanded PTFE, the outer layer need not necessarily be made of this material. Expanded PTFE is preferred as the inner material as this is a suitable graft material enabling ingrowth of endothelium. The outer layer may however preferably be made from a material which has improved strength and may be made from thinner material hence reducing the size of the device further. Suitable materials include nylon, polyethylene, polypropylene, polyurethane, polyvinylchloride and various fluoropolymers. The outer layer may even have the property of thrombogenicity which may be desirable as this would help to thrombose the aneurysm sac. A thromogenic material would encourage the blood in the aneurysm sac, outside the graft, to clot. Suitable thrombogenic coating materials include collagen, polysaccharides and blood clotting factors (e.g. thrombin and fibrinogen). This is beneficial, as it encourages the aneurysm sac to shrink and resolve. It is also possible to form the graft with small perforations, not within the region of the inflatable member, which would allow ingrowth onto the PTFE from the outside of the graft.

One major problem with aortic stent grafts in general is the requirement for a neck of normal aorta below the renal arteries. This is used to facilitate the placement of the device and produces a seal. It is often the absence of a suitable neck that prevents the use of a stent graft from being attempted or results in failure of the device. This may occur at the time of placement, soon after or even months later.

The present invention enables the treatment of abdominal aortic aneurysms by a stent graft mechanism extending from the infra-renal segment of the aorta to either the distal aorta or into one of the iliac arteries. Via this technique, it may be possible to cross the renal arteries with graft material and subsequently revascularise the kidneys. An additional application may also be the treatment of thoracic aneurysms.

The possibility of providing a stent graft structure across the renal arteries so that their origins are covered by the graft material and then revascularising the kidneys is therefore a preferred function. It may be possible to achieve this with the present system because the graft material is very thin. Revascularisation would be achieved by percutaneous puncture in a branch of the renal artery within the kidney and puncturing the graft material from the renal side into the aorta. Angioplasty and then stenting of the renal artery origin at this point would be performed from the groin re-establishing renal blood flow.

DETAILED DESCRIPTION OF PREFERRED EMBODIMENTS

Preferred embodiments of the invention will now be described by way of example with reference to the drawings in which.

Figure 1:
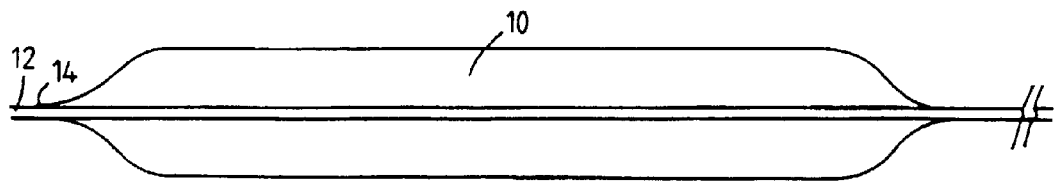
FIG. 1 is a side view of a conventional angioplasty balloon showing a balloon member inflated.

FIG. 1 shows a prior art angioplasty balloon 10 in an inflated form. At one end 14 of the balloon 10 a catheter 12 is fused to the balloon 10. Due to this fusion, such an angioplasty balloon is not suitable for the present invention as disconnection of the catheter 12 from the balloon 10 will cause the balloon 10 to rupture.

Figure 2:
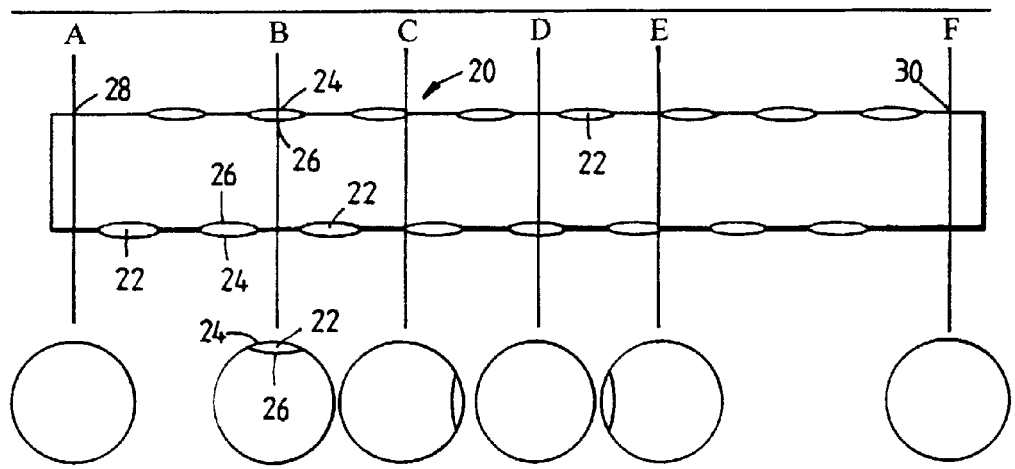
FIG. 2 is a side view of a collapsible stent graft according to the present invention, comprising a spiral inflatable member and showing cross-sectional representations.

In FIG. 2, is shown a stent graft 20 according to the present invention with a spiral inflatable member 22 capable of inflation formed from an inner tubular member 26 and an outer layer 24. The inflatable graft 20 comprises two fused ends 28, 30. Between alternate turns of the spiral inflatable member 22 the inner tubular member 26 and outer layer 24 are fused or adhered together. This fusion occurs by any suitable method, such as, adhesive bonding, welding, heat sealing or ultrasonic sealing. Longitudinal and transverse cross-sectional representations of the spiral inflatable member 22 are shown. The solid black line in FIG. 2 shows the inner tubular member 26 and outer layer 24 fused together in such a way as to provide the spiral inflatable member 22 between two fused ends 28, 30. At cross-sections A, B, C, D, E and F along the spiral inflatable member, representations show the arrangement of the inflatable member 22.

Figure 3:
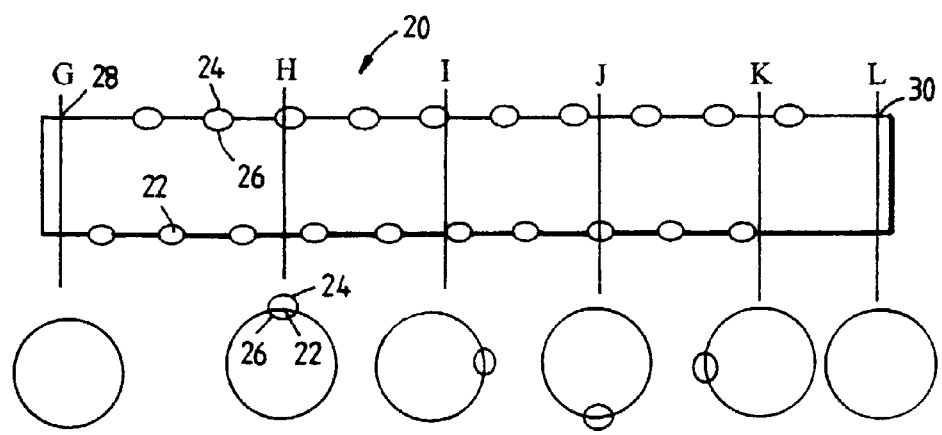
FIG. 3 is a side view of the collapsible stent graft as shown in FIG. 2 inflated and also shows cross-sectional representations.

In FIG. 3, the spiral inflatable member 22 is shown inflated. The graft is inflated by injecting a suitable material into the inflatable member 22. The inflatable member 22 is connected at the distal end of the graft (that is the femoral end and the end nearest to where the graft is introduced into the femoral artery, with the graft in position within the aortic aneurysm) to a fine bore catheter tube of 1 mm diameter (3 French gauge) through which a fluid-like material is injected. This requires a detachable valve mechanism to be located near the junction between the fine bore catheter and the inflatable member 22 to allow the fine bore catheter tube to be disconnected and for the inflatable member 22 to remain inflated without leakage. Alternatively, inflation could be initiated at the proximal end (the forward end) of the graft via separate catheter tube. The inflatable member 22 of the graft 20 acts like a spring system to extend the collapsed tubular member. On inflation the graft forms a predetermined shape. This predetermined shape may be tubular as shown in the Figures or bifurcated. The fused sections of the graft 20 between the turns of the inflated member 22 allows flexibility and prevents kinking and the development of dissection.

Figure 4:
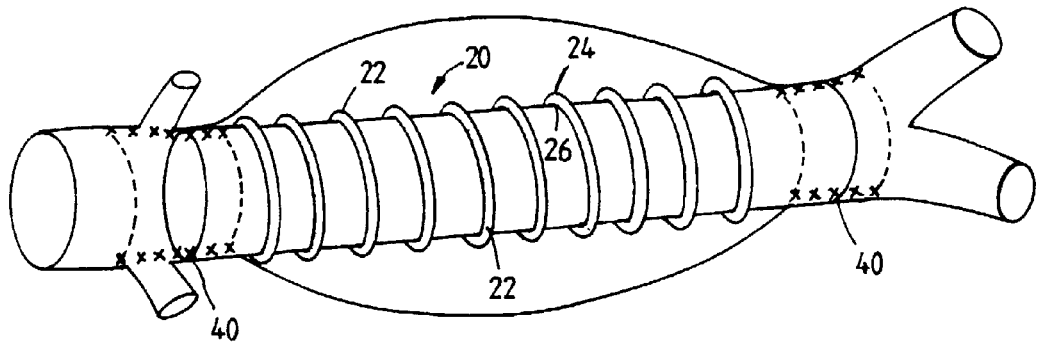
FIG. 4 is a view of the inflated device and how it fits into an infra-renal aorta.

FIG. 4 is a three-dimensional representation of the graft 20 in an inflated form in place in an infra-renal aorta. Stents 40 at each end hold the graft in place.

Figure 5:
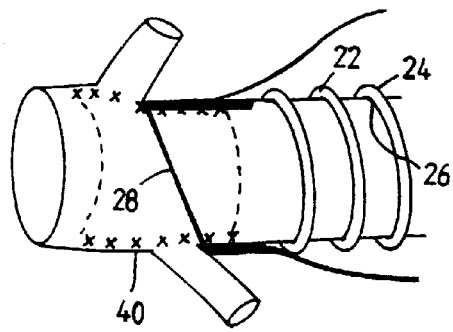
FIG. 5 is a representation of a preferred configuration of the upper end of a stent graft used to accommodate an asymmetric renal artery and to maximise the contact between the graft and aorta at this site.
Figure 6:
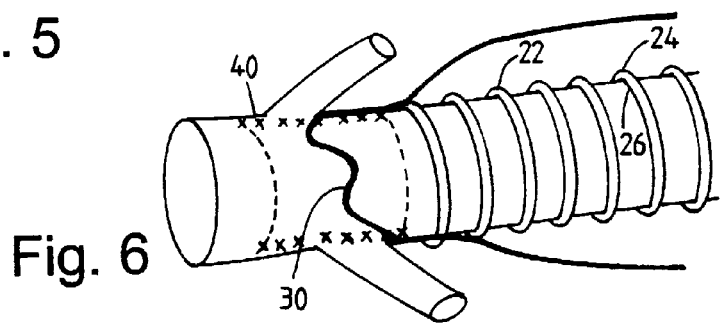
FIG. 6 is a representation of a further preferred angled configuration of the upper end of a stent graft used to accommodate an asymmetric renal artery and to maximise the contact between the graft and aorta at this site.

FIGS. 5 and 6 show possible configurations of an upper end 28, 30 of the graft 20 to accommodate asymmetric renal artery origins and to maximise the contact between the graft 20 and aorta at this site.

Figure 7:
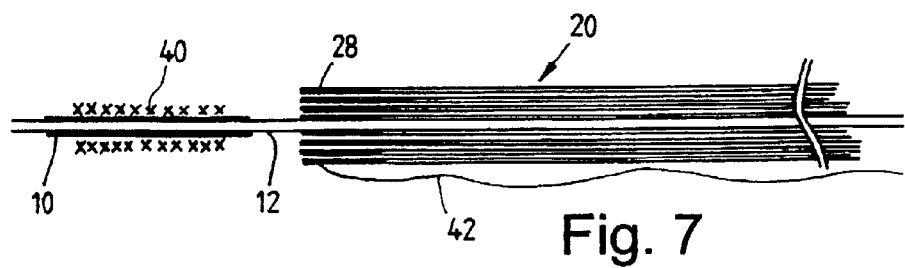
FIG. 7 is a schematic representation of an assembly for insertion into an aorta of a patient.

FIG. 7 shows an assembly ready for introduction into an artery and comprising an angioplasty balloon 10 of the type shown in FIG. 1 located within an expandable stent 40 (e.g. Palmaz stent). A collapsed stent graft 20 according to the present invention is located around catheter 12 of the angioplasty balloon behind the stent. Alternatively, a self-expanding stent (e.g. a Wall stent or a Nitonol stent) could be employed. A sheath (not shown) may be provided around the assembly to facilitate insertion into the artery.

The insertion procedure is as follows. The assembly is introduced into the artery until the forward end 28 of the graft is in the correct position. The sheath (if any) is then partially retracted to reveal the forward end of the graft, which is then partially inflated by introduction of liquid into the forward end thereof through a catheter tube 42 removably attached thereto.

This expands the forward end of the graft into contact with the artery wall and locates the graft in place.

The catheter is then partially withdrawn until the stent lies within the expanded forward end 28 of the graft. The angioplasty balloon is inflated to expand the stent to secure the graft to the arterial wall.

The sheath is then fully retracted to allow the rest of the graft to be inflated (after first removing the tube 42 if required). The angioplasty balloon is removed. The rearward end of the graft may then be stented in place in similar manner. Any tube attached to the rearward end of the inflatable member is now removed to leave the member in the inflated state.

Figure 8:
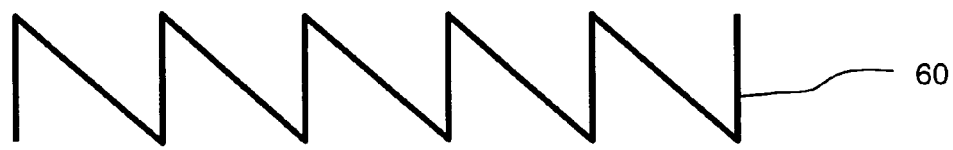
FIG. 8 depicts a zig-zag pattern.
Figure 9:
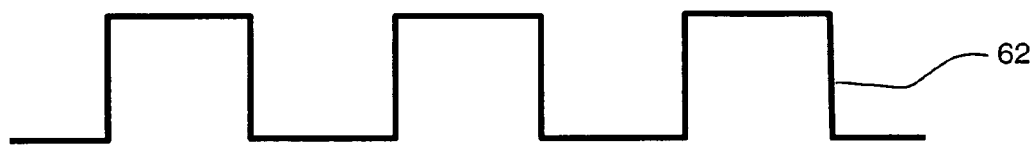
FIG. 9 depicts a square-wave pattern.

The inflatable member 22 may also take a variety of other shapes such as a zig-zag pattern 60 as depicted in FIG. 8 or square-wave pattern 62 as depicted in FIG. 9 around the tubular member 26.

The invention claimed is:

1. A collapsible stent graft for lining a blood vessel comprising:
   a collapsible inner tubular member having a proximal and a distal end and comprising expanded PTFE;
   an outer sleeve layer co-extensive with the inner tubular member and having a proximal and a distal end and comprising PTFE and disposed around the inner tubular member, the distal end of the outer layer being fused to the distal end of the inner tubular member, the proximal end of the outer layer being fused to the proximal end of the inner tubular member, and the outer layer attached to the inner tubular member at localized attachment points so as to define an inflatable member extending around the inner tubular member in a plurality of turns and attached thereto, wherein the inflatable member is expandable by inflation so that the inflatable member expands the inner tubular member from a collapsed state to an expanded state;
   a metallic stent disposed at the distal or proximal end of the fused collapsible inner tubular member and the fused outer sleeve layer;
   an inflation tube integrally formed between the outer sleeve layer and the inner tubular member for inflating the inflatable member; and
   hooks disposed on the metallic stent, the hooks being distal from the inflatable member.

2. The stent graft of claim 1, wherein said outer layer further comprises a thrombogenic material.

3. The stent graft of claim 2, wherein the thrombogenic material is selected from the group consisting of a collagen, a polysaccharide, and a blood clotting factor.

4. The stent graft of claim 3, wherein the thrombogenic material is the blood clotting factor.

5. The stent graft of claim 4, wherein the blood clotting factor is thrombin or fibrinogen.

6. The stent graft of claim 1, wherein the inflatable member forms a spiral structure around the tubular member.

7. The stent graft of claim 1, further comprising a spacing of 1 or 2 mm between adjacent turns.

8. The stent graft of claim 1, comprising a plurality of inflatable members.

9. The stent graft of claim 1, wherein the inflatable member comprises a zig-zag or square-wave pattern.

10. The stent graft of claim 1, comprising perforations distal from the inflatable member to allow tissue ingrowth thereinto.

11. The stent graft of claim 1, wherein the tubular member has a wall thickness thinner than 0.2 mm.

12. The stent graft of claim 1, wherein an end of the inner tubular member is of undulating shape.

13. The stent graft of claim 1, wherein an end of the inner tubular member is angled.

14. The stent graft of claim 1, wherein the inner tubular member is bifurcated.

15. The stent graft of claim 1, further comprising a liquid for inflation of the inflatable member.

16. The stent graft of claim 15, wherein the liquid solidifies after injection into the inflatable member.

17. The stent graft of claim 16, wherein the solidified liquid adheres to the inside walls of the inflatable member.

18. The stent graft of claim 1, wherein the inner tubular member comprises expanded PTFE film having a microstructure selected from the group consisting of uni-axially oriented fibrils, bi-axially oriented fibrils, or multi-axially oriented fibrils.

19. A collapsible stent graft for lining a blood vessel comprising:
- a collapsible inner tubular member having a proximal and a distal end and comprising a material of expanded PTFE;
- an outer sleeve layer having a proximal and a distal end and comprising a material different from the material of the inner tubular member and disposed around the inner tubular member, the distal end of the outer layer being fused to the distal end of the inner tubular member, the proximal end of the outer layer being fused to the proximal end of the inner tubular member, and the outer layer attached to the inner tubular member at localized attachment points so as to define an inflatable member extending around the inner tubular member in a plurality of turns and attached thereto, wherein the inflatable member is expandable by inflation so that the inflatable member expands the inner tubular member from a collapsed state to an expanded state;
- a metallic stent disposed at the distal or proximal end of the fused collapsible inner tubular member and the fused outer sleeve layer; and
- hooks disposed on the metallic stent, the hooks being distal from the inflatable member;
- wherein the material for the outer sleeve layer comprises PTFE.

20. The stent graft of claim 19, wherein the material for the outer sleeve layer has a greater strength to resist tearing than the material for the inner tubular member.

21. The stent graft of claim 19, wherein said outer sleeve layer further comprises a coating of a thrombogenic material.

22. The stent graft of claim 21, wherein the thrombogenic material is selected from the group consisting of a collagen, a polysaccharide, and a blood clotting factor.

23. The stent graft of claim 22, wherein the thrombogenic material is the blood clotting factor.

24. The stent graft of claim 23, wherein the blood clotting factor is thrombin or fibrinogen.

25. The stent graft of claim 19, comprising a plurality of inflatable members.

26. The stent graft of claim 19, wherein the tubular member has a wall thickness thinner than 0.2 mm.

27. The stent graft of claim 19, wherein the inner tubular member is bifurcated.

28. The stent graft of claim 19, further comprising a liquid for inflation of the inflatable member.

29. The stent graft of claim 28, wherein the liquid solidifies after injection into the inflatable member.

\* \* \* \* \*